(12) United States Patent
Stammberger et al.

(10) Patent No.: US 9,357,986 B2
(45) Date of Patent: Jun. 7, 2016

(54) MEDICAL INSTRUMENT FOR DILATING OSSEOUS STRUCTURES

(75) Inventors: Heinz Stammberger, Graz (AT); Martin Blocher, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 938 days.

(21) Appl. No.: 12/768,420

(22) Filed: Apr. 27, 2010

(65) Prior Publication Data

US 2010/0274275 A1   Oct. 28, 2010

(30) Foreign Application Priority Data

Apr. 27, 2009   (DE) .......................... 10 2009 018 723

(51) Int. Cl.
| | | |
|---|---|---|
| *A61M 29/00* | (2006.01) | |
| *A61B 17/02* | (2006.01) | |
| *A61B 17/88* | (2006.01) | |
| *A61B 17/16* | (2006.01) | |
| *A61B 17/24* | (2006.01) | |
| *A61B 17/00* | (2006.01) | |
| *A61B 17/32* | (2006.01) | |

(52) U.S. Cl.
CPC ......... *A61B 17/0218* (2013.01); *A61B 17/1688* (2013.01); *A61B 17/24* (2013.01); *A61B 17/8858* (2013.01); *A61B 17/025* (2013.01); *A61B 2017/00367* (2013.01); *A61B 2017/320044* (2013.01)

(58) Field of Classification Search
CPC ............. A61B 17/885; A61B 17/8855; A61B 17/8858; A61B 17/1671; A61B 2017/320044; A61B 2017/3932
USPC ............................ 606/90, 191, 198, 205–208
See application file for complete search history.

(56) References Cited

U.S. PATENT DOCUMENTS

| | | | | |
|---|---|---|---|---|
| 4,648,402 A | * | 3/1987 | Santos | .......................... 606/198 |
| 5,172,700 A | * | 12/1992 | Bencini | .................. A61B 10/06 600/564 |

(Continued)

FOREIGN PATENT DOCUMENTS

| | | |
|---|---|---|
| DE | 69120325 T2 | 12/1996 |
| EP | 1112103 B1 | 1/2006 |

(Continued)

OTHER PUBLICATIONS

German Search Report; 10 2009 018 723.5; Jan. 13, 2010; 4 pages.

(Continued)

*Primary Examiner* — Katherine Rodjom
(74) *Attorney, Agent, or Firm* — Whitmyer IP Group LLC

(57) ABSTRACT

A medical instrument for dilating osseous structures, with a shaft on whose distal end a tool point is positioned and on whose proximal end a handle is positioned, such that the handle and the tool point are in active connection with one another by means of an actuating element in such a way that by actuating the handle the tool point can spread radially at least partially and where the distal end of the actuating element has a thickened configuration. To provide a dilating instrument that is sufficiently stable and allows for sensitive actuation, it is proposed with the invention that the tool point should consist of several segments that can radiate radially outward and enclose the thickened distal end of the actuating element essentially completely, when the tool point is in the closed position.

13 Claims, 6 Drawing Sheets

(56) References Cited

U.S. PATENT DOCUMENTS

| | | |
|---|---|---|
| 6,706,052 B1 * | 3/2004 | Chin ............................ 606/198 |
| 2003/0023260 A1 | 1/2003 | Bonutti |
| 2004/0049207 A1 * | 3/2004 | Goldfarb ............ A61B 17/0401 606/139 |
| 2004/0077999 A1 * | 4/2004 | Selmon et al. ................. 604/104 |
| 2006/0079925 A1 * | 4/2006 | Kerr ............................. 606/198 |
| 2006/0089627 A1 * | 4/2006 | Burnett ............ A61B 17/12099 606/1 |
| 2007/0135686 A1 | 6/2007 | Pruitt, Jr. et al. |
| 2007/0287598 A1 * | 12/2007 | Christensen, III .............. 482/11 |
| 2009/0024158 A1 | 1/2009 | Viker |

FOREIGN PATENT DOCUMENTS

| | | |
|---|---|---|
| WO | 9917661 A1 | 4/1999 |
| WO | 2007070567 A2 | 6/2007 |
| WO | 2008042155 A2 | 4/2008 |
| WO | 2008134288 A2 | 11/2008 |

OTHER PUBLICATIONS

European Search Report; Application No. EP 10 00 4247; Aug. 4, 2010; 5 pages.

* cited by examiner

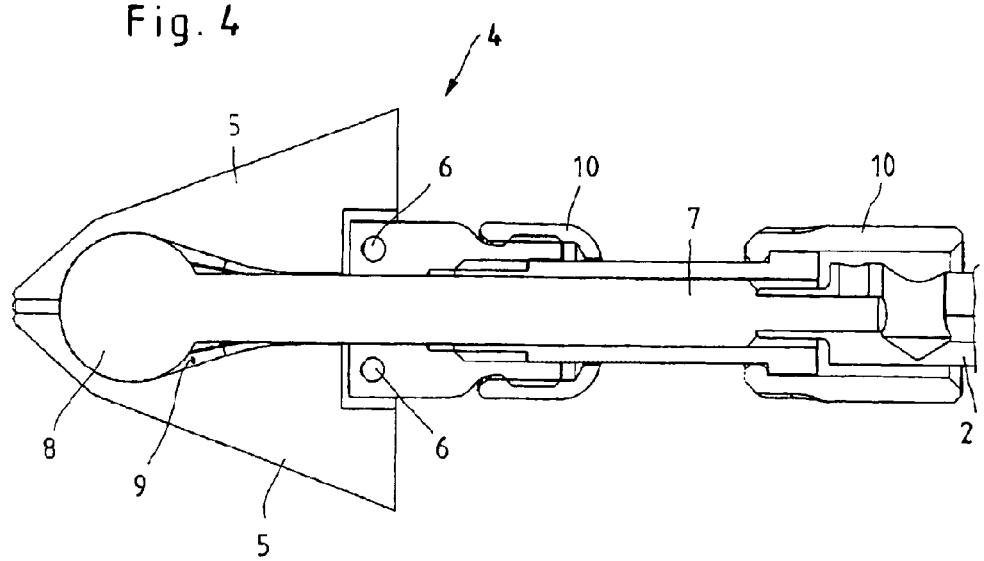
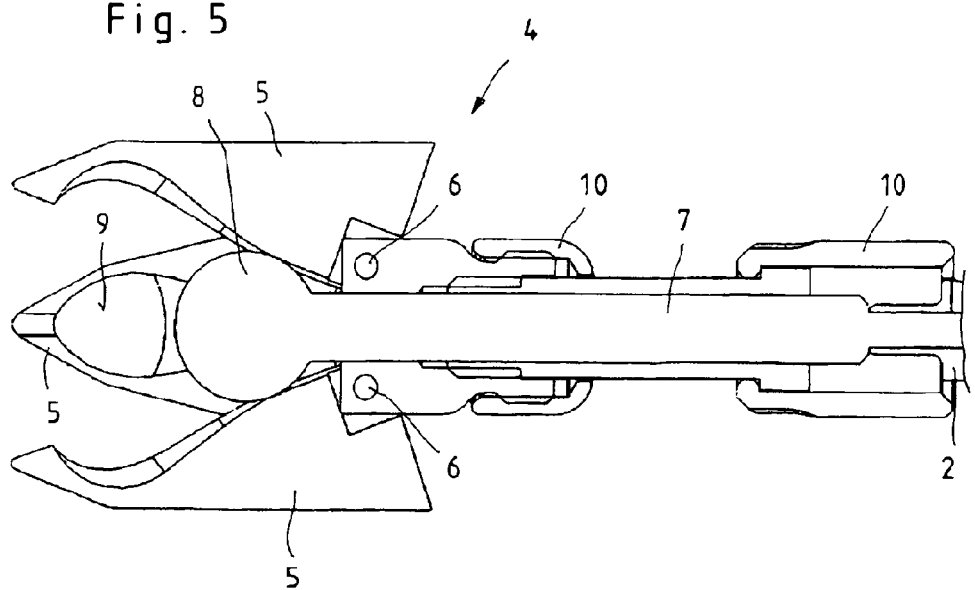

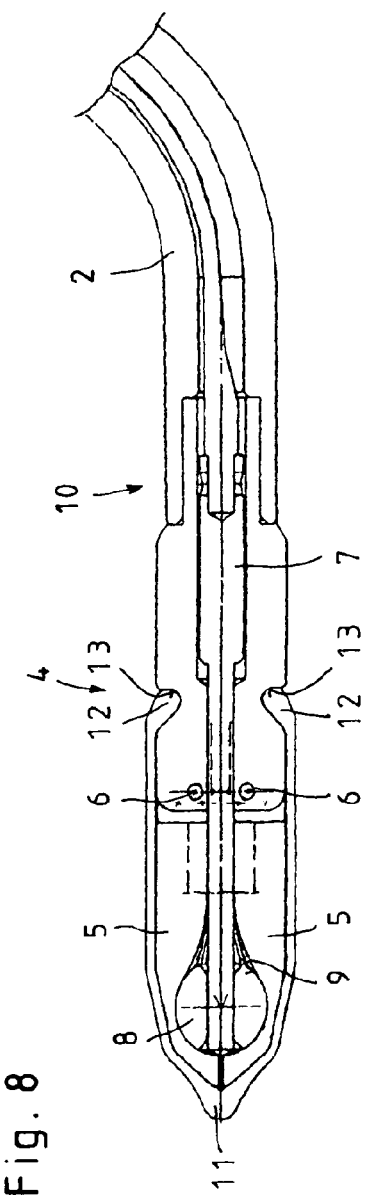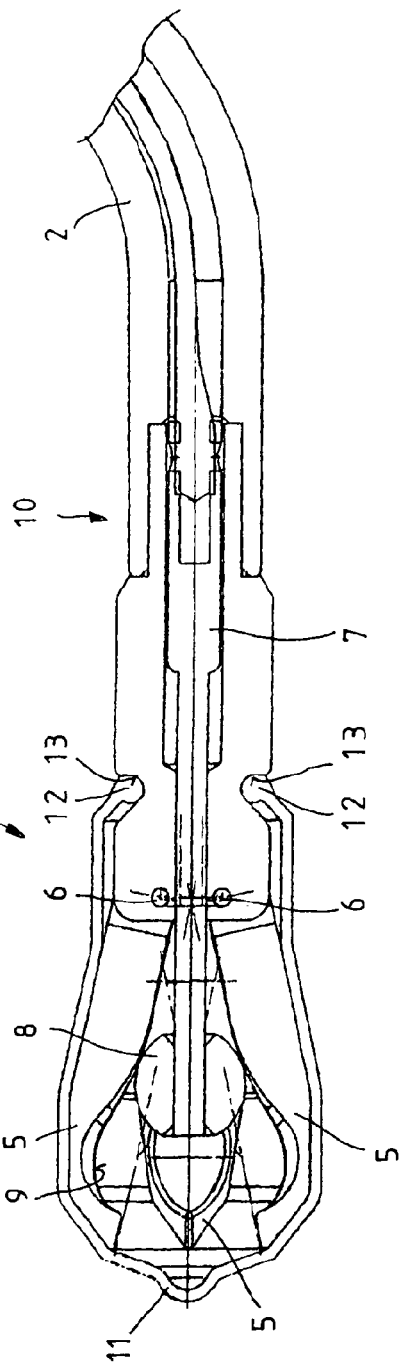

MEDICAL INSTRUMENT FOR DILATING OSSEOUS STRUCTURES

CROSS-REFERENCE TO RELATED APPLICATIONS

The present application claims priority of German patent application No. 10 2009 018 723.5 filed on Apr. 27, 2009, the content of which is incorporated herein by reference.

FIELD OF THE INVENTION

The invention relates to a medical instrument for dilating osseous structures, with a shaft on whose distal end a tool point is positioned and on whose proximal end a handle is positioned, such that the handle and tool point are in active connection with one another by means of an actuating element in such a way that, by actuating the handle, the tool point can be radially widened at least partially and such that the distal end of the actuating element has a thickened form.

BACKGROUND OF THE INVENTION

According to the invention, dilating instruments are used, for instance, in endoscopic ENT surgery for widening a patient's frontal sinus and removing osseous growths in the frontal sinus.

A generic medical dilating instrument is disclosed, for instance, in WO 2008/134288 A2. In a first embodiment of this known dilating instrument, the tool point consists of several lamellae, which are bound together distally and are compressed together by means of the actuating element in such a way that the lamellae widen radially in a balloon-like manner. This construction is especially suited for spreading soft tissue, but the lamellae buckle inward when they are used for removing osseous growths.

According to a second embodiment of this known dilating instrument, the tool point consists of several lamellae that are not bound together on the distal end and can be bent open radially by means of a thickening on the distal end of the actuating element. The disadvantage of this embodiment is that the tool point is open even when the lamellae of the tool point are in the non-spread position, so that tissue can penetrate into the dilating mechanism. In addition, the elastically bendable lamellae allow the user only a limited tactile control in the functioning of the tool point.

In addition, instruments for dilating heart vessels are known that can widen vessels and penetrate through vessel closures. These known medical instruments for widening vessels, however, are only suited for transmitting minor forces, in order to prevent injury to the vessels that are to be widened. These known instruments, however, are not suited for dilating osseous growths such as in the frontal sinus.

On this basis it is the object of the invention to provide a dilating instrument that is of sufficient stability and also allows sensitive actuation.

SUMMARY OF THE INVENTION

The solution to this object, according to the invention, is characterized in that the tool point consists of several segments that can pivot radially outward and that enclose the thickened distal end of the actuating element essentially completely when the tool point is in the closed position.

As a result of this configuration of the tool point with the pivotable segments that completely enclose the distal end of the actuating element, the inventive tool point, when the segments are in closed position, is completely closed with respect to the outside, so that the dilating mechanism is also protected. In addition, the pivotable segments can be configured as form-stable pivoting elements that allow both great widening strength and sensitive actuation by the operator.

In advantageous manner, the pivotable segments of the tool point completely enclose the thickened distal end of the actuating element when the tool point is in closed position; but because of manufacturing standards and tolerances, minimal gaps can also remain between the pivotable segments although they pose no threat to the inventive essentially complete enclosing of the thickened distal end of the actuation element.

According to a preferred embodiment of the invention, it is proposed for configuring the dilation mechanism that an insertion space should be configured for the thickened distal end of the actuation element in the interior of the tool point configured by the individual segments, so that the inner contour of the individual segments of the tool point is configured in such a way that, in a displacement of the thickened distal end of the actuating element, the segments pivot radially outward. As a result of the displacement of the actuating element, advantageously configured as a push-pull rod, in the axial direction of the shaft, the pivotable segments of the tool point are pressed radially outward.

The insertion space for the thickened distal end of the actuating element is advantageously configured so that it narrows conically toward the proximal end of the segments, so that when the actuating element is withdrawn in the proximal direction, the segments are automatically pivoted outward and open the distal end of the tool point in the form of a tulip blossom.

The thickened distal end of the actuation element, according to a practical embodiment of the invention, is spherical or conical in configuration.

According to a first inventive embodiment, it is proposed that the tool point should consist of four pivotable segments, each of which is jointed at a 90-degree angle to the others on the proximal end of the tool point.

To facilitate non-traumatic insertion of the tool point into the surgical area, it is proposed with the invention that the outer contour of the distal end of the segments of the tool point should be configured to taper conically when the tool point is in closed position. In addition to the conical configuration of only the distal end of the tool point, with an alternative embodiment it is proposed that the entire outer contour of the segments of the tool point should be configured to taper conically toward the distal end in several stages when the tool point is in closed position.

In addition, with a practical embodiment of the invention it is proposed that the outer sides of the segments of the tool point, with the tool point in opened position, should be configured to run essentially parallel to one another. This parallel configuration of the sides of the pivotable segments when the tool point is in the opened working position is advantageous in order to prevent any slippage outward of the tool point into areas of the surgical area that are not yet examined.

Because the tool point, especially in removing osseous growths, is exposed to steady abrasion, it is proposed with the invention that the tool point should be removably connected with the shaft.

The assembly and disassembly of the instrument, according to the invention, can be facilitated if the portion of the actuating element positioned in the tool point is coupled removably with the portion of the actuating element positioned in the shaft by means of a coupling mechanism.

It is finally proposed with the invention that the tool point should be coverable with an elastic casing of synthetic material in order to prevent penetration of tissue into the dilating mechanism.

It is further proposed with the invention that the pivotable segments of the tool point should be movable from the opened position of the tool point back into the closed position of the tool point by means of the elastic synthetic casing. In this embodiment the return force of the elastic synthetic casing is used in order to move the tool point back into the closed position after the widening of the pivotable segments and the related stretching of the synthetic casing.

To configure the elastic synthetic casing, it is proposed with the invention that the elastic synthetic casing should take the form of a covering that is open at the proximal end and has a surrounding insulating element configured on its proximal edge.

The insulating element should advantageously be configured as a surrounding thickening, which can be affixed in a corresponding surround groove of the tool point.

Additional properties and advantages of the invention can be seen from the appended illustrations, in which five embodiments of an inventive medical dilating instrument are presented only in exemplary manner, without restricting the invention to these examples.

BRIEF DESCRIPTION OF THE DRAWINGS

FIG. 4 shows a cut-out side view of a second embodiment of a tool point in closed position.

FIG. 5 shows a side view of the tool point according to FIG. 4, but showing the opened position.

FIG. 8 shows a cut-out side view of a fifth embodiment of a tool point in closed position.

FIG. 9 shows a side view of the tool point according to FIG. 8, but showing the opened position.

DETAILED DESCRIPTION OF THE INVENTION

Figure 1:
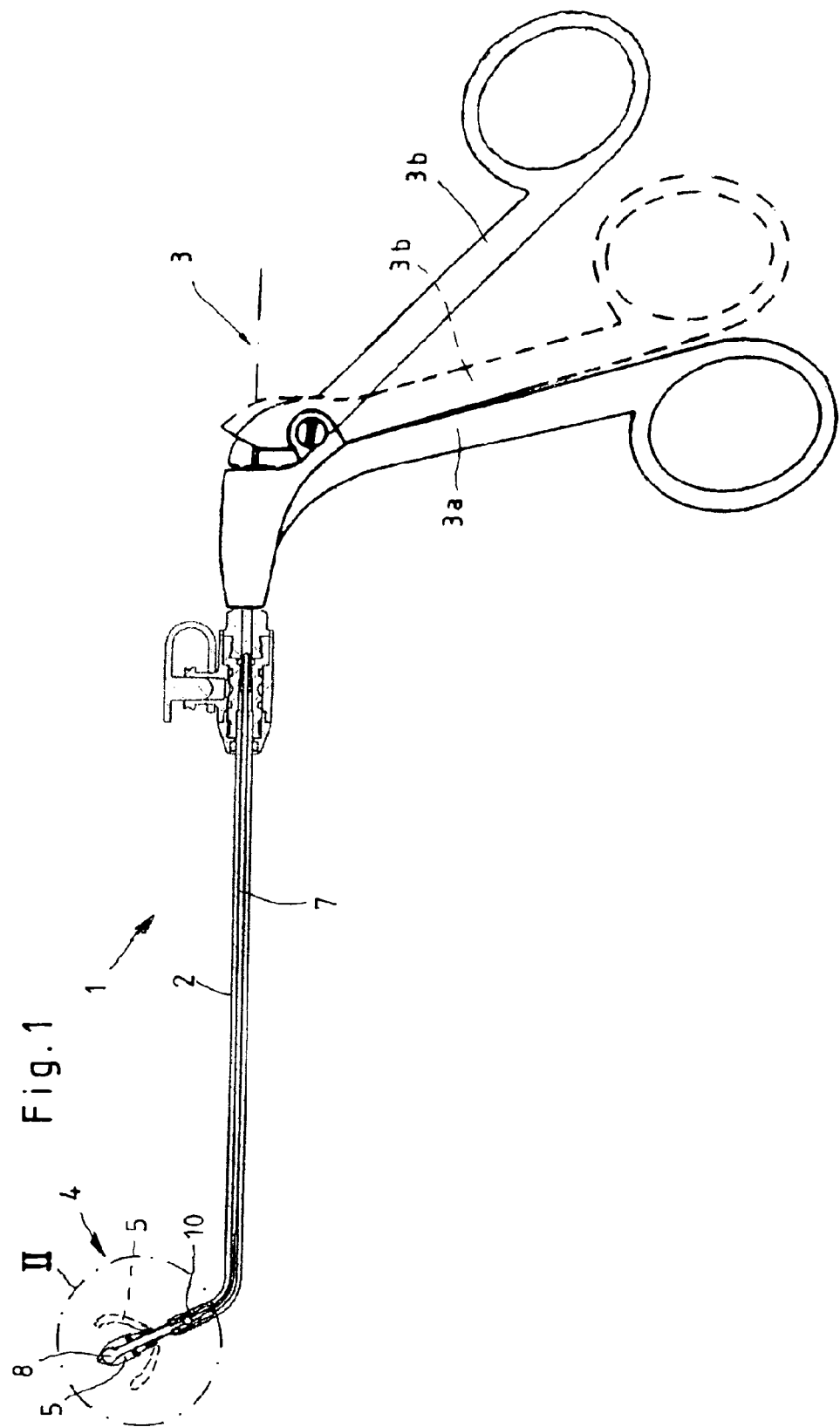
FIG. 1 shows a schematic, partly cut-out side view of an inventive medical dilating instrument.

The medical dilating instrument 1 shown schematically in FIG. 1 consists essentially of a hollow shaft 2 on whose proximal end a handle 3 is positioned that in the illustrated embodiment consists of a rigid gripping member 3*a* and a gripping member 3*b* that can pivot with respect to the rigid gripping member 3*a*. Positioned on the distal end of the shaft 2 is a tool point 4, which, as can be seen in particular from FIG. 3, consists of several segments 5, which are mounted on the proximal end of the tool point 4 so that they can pivot radially outward around the pivot axis 6.

As can further be seen from FIG. 1, the tool point 4 and the pivotable gripping member 3*b* of the handle 3 are in active connection with one another by means of an actuating element 7 that is mounted so that it can slide axially within the hollow shaft 2 and is configured as a pull rod, in such a way that moving the gripping member 3*b* of the handle 3 causes the pivoting of the segments 5 of the tool point 4 from the closed position (hatch-marked depiction in FIG. 1 as well as in FIGS. 2, 4, 6, and 7) into position (dotted depiction in FIG. 1 as well as FIGS. 3 and 5) or vice versa. The resulting position of the pivotable gripping member 3*b* of the handle 3 in each case in FIG. 1 is likewise illustrated as hatch-marked (for the closed position) and dotted (for the opened position).

Alternatively to the illustrated configuration of the actuating element 7 as a pull rod, it is also possible of course to configure the mechanism of the dilating instrument 1 in such a way that the actuating element 7 can take the form of a push rod.

In the illustrated embodiments, the tool point 4 consists in each case of four segments 5, which are positioned at 90-degree angles to one another so that they can pivot on the proximal end of the tool point 4. It is also possible of course to construct the tool point 4 to consist of more or fewer segments 5, for instance as having three segments 5, which are positioned at 120-degree angles to one another so that they can pivot on the proximal end of the tool point 4.

Figure 2:
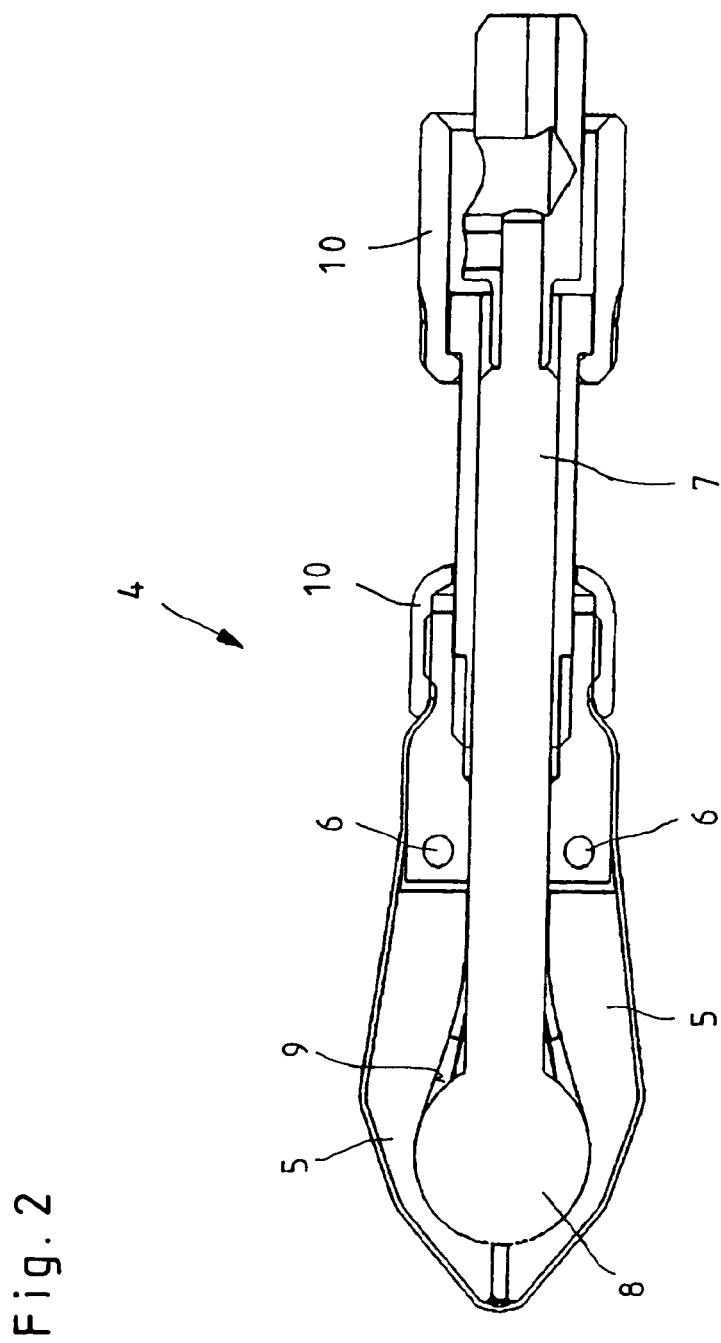
FIG. 2 shows an enlarged depiction of detail II, showing a first embodiment of a tool point in the closed position.

The pivotable segments 5 of the tool point 4 are always positioned and configured in such a way that, when the tool point 4 is in closed position, they form a closed outer contour and, as can be seen from FIG. 2, they essentially completely enclose the distal end 8 of the actuating element 7.

The term "essentially completely enclose" is to be understood to mean that, because of manufacturing standards and tolerances, minimal gaps can also remain between the pivotable segments although they pose no threat to the required enclosing of the thickened distal end of the actuating element. However, with the tool point in closed position, the pivotable segments of the tool point advantageously enclose the thickened distal end of the actuating element, completely and free of gaps.

To allow the dilating instrument 1, with the tool point 4 in front, to penetrate non-traumatically into the surgical area, for instance into a front sinus, the outer contour of the distal end of the segments 5 of the tool point 4 is also configured in all embodiments, with the tool point 4 in closed position, as tapering conically.

The embodiments illustrated in FIGS. 1 through 7 are distinguished from one another by the configuration of the outer contour of the tool point 4, which presents them with the segments in the closed and/or opened position.

Figure 3:
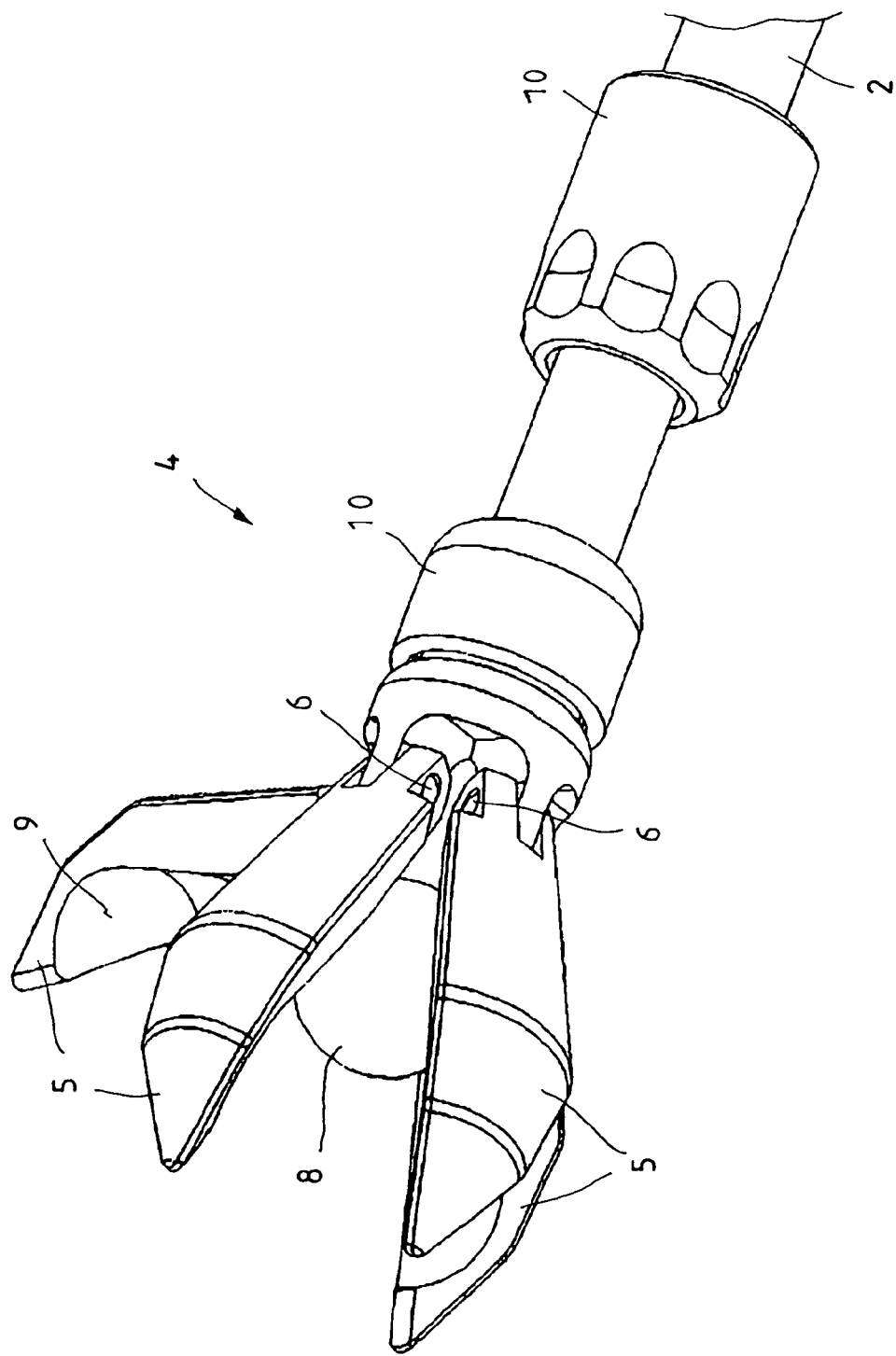
FIG. 3 shows a non-cut-out perspective view of the depiction in FIG. 2, but showing the tool point in opened position.

In the first embodiment, shown in FIGS. 1 through 3, the tool point 4 has a double-conical configuration in such a way that it widens at first in the direction going from the pivot axis 6 in the distal direction and then, in turn, tapers conically toward the distal end of the tool point 4.

Figure 6:
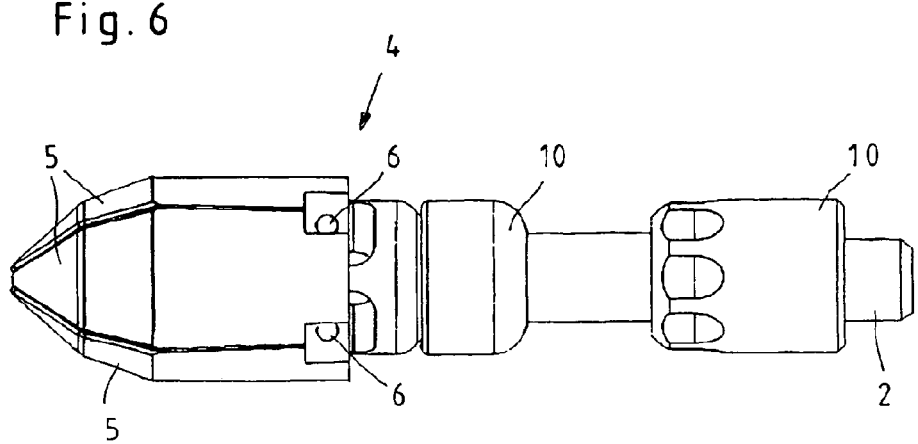
FIG. 6 shows a side view of a third embodiment of a tool point in closed position.

The second embodiment for configuring the tool point 4, seen in FIGS. 4 and 6, is distinguished from the previously described embodiment primarily in that the outer sides of the segments 5 of the tool point 4, with the tool point 4 in opened working position, are configured to run essentially parallel to one another.

This parallel configuration of the sides of the pivotable segments 5 in opened working position is advantageous in order to ensure the ability to prevent the tool point 4 from slipping away into portions of the surgical area not yet examined, when the tool point 4 of the dilating instrument 1 is moved back and forth by the operator to widen the surgical area and break up osseous growths.

In the third embodiment, shown in FIG. 6, the outer sides of the segments 5 of the tool point 4, with the tool point 4 in closed position, are configured to run essentially parallel to one another and only point toward one another while tapering conically at the distal end of the tool point 4.

Figure 7:
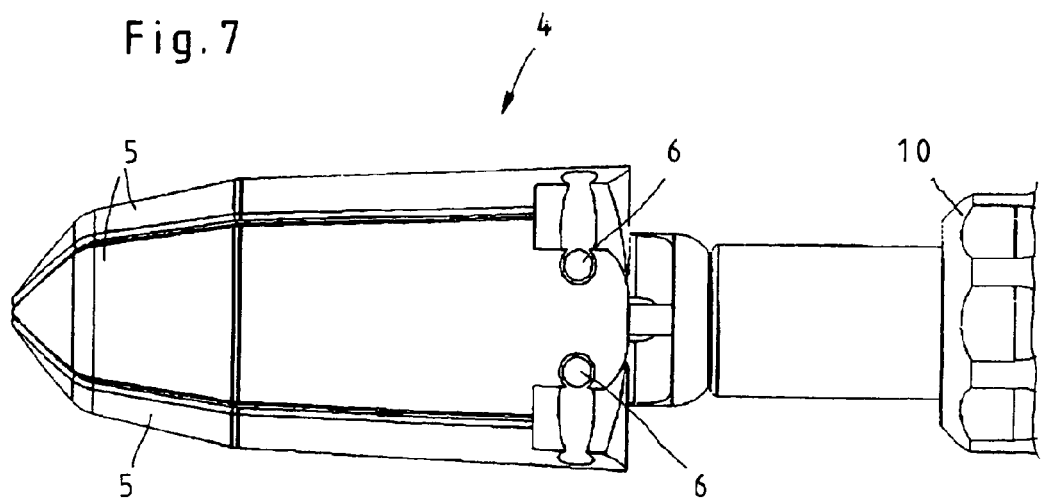
FIG. 7 shows a side view of a fourth embodiment of a tool point in closed position.

FIG. 7, finally, shows a fourth embodiment for configuring the outer contour of the tool point 4, in which the outer contour of the segments 5 of the tool point 4, with the tool point in closed position, is configured as tapering conically in several stages toward the distal end.

Because the tool point 4 or the pivotable segments 5 of the tool point 4 are subject to a certain abrasion from use, the illustrated embodiments of the dilating instrument 2 are configured in such a way that the tool point 4 can be removably affixed to the shaft 2 by means of a coupling mechanism 10.

Likewise, in the embodiment shown in FIG. 2, the portion of the actuating element 7 mounted in the tool point 4 is removably coupled with the portion of the actuating element 7 mounted in the shaft 2 by means of a coupling mechanism 10. It is also possible of course to produce the actuating element 7 as a single piece in such a way that it can be inserted from the distal end into the opened tool point 4 and the shaft 2.

The dilating instrument 1 described above is employed in endoscopic surgery in the following way:

Starting with the tool point 4 in closed position as shown in FIG. 1 (hatch-marked line) as well as FIGS. 2, 4, 6, and 7, the dilating instrument 1 is inserted into the surgical area, in particular into a patient's sinus cavity, with the tool point 4 in front, in order then to widen constricted sections.

To widen constricted sections of the surgical area, including for the removal of osseous growths, the operator shifts the pivotable member 3b of the handle into the position shown with dots in FIG. 1, so that the actuating element 7 coupled with this gripping member 3b is pulled in the proximal direction. On the distal end, pulling back the actuating element 7 in the proximal direction causes the segments 5 of the tool point 4 to be pivoted radially outward by means of the thickened distal end 8 of the actuating element 7 into the tool point's 4 opened working position as shown in FIG. 1 (dotted line) as well as FIGS. 3 and 5.

In contrast to the construction of the tool points from individual lamellae as known in the art, in the previously described structure of the tool point 4 the individual pivotable segments 5 that are to be opened by the thickened distal end 8 of the actuation element 7 can be configured as clearly more massive and thus more form-stable, so that the points of the segments 5 can also be employed for widening and breaking up growths. Thanks to this feature, the spreading surface of the tool point 4 as well as the diameter of the opened tool point 4 can be made larger.

In addition, the mechanical spreading force in the described configuration of the tool point 4 is not dependent on the flexing strength of individual lamellae, but is instead based purely on the force transmission by means of the leverages applied.

To prevent the penetration of tissue into the tulip-shaped opened tool point 4, it is additionally possible to cover the tool point 4 with an elastic synthetic casing 11 as is shown in FIGS. 8 and 9. But even without such a covering, the described dilation mechanism can be applied without problem because the simple and stable structure ensures good and rapid cleaning of all components.

As can be seen from FIGS. 8 and 9, the synthetic casing 11 is configured as a covering that is open on the proximal end and can be pulled starting from the distal side over the tool point 4. On the proximal end the synthetic casing 11 has a surrounding insulating element 12, which is contiguous with the tool point 4 and insulates it in order to prevent the penetration of tissue and/or fluid under the synthetic casing 11 and thus into the interior of the tool point 4. In the illustrated embodiment the insulating element 12 takes the form of a surrounding bulge-like thickening, which can be affixed in a corresponding surrounding groove 13 of the tool point 4.

Affixing the synthetic casing 11 in the groove, in addition, has the advantage that it prevents the synthetic casing 11 from being pulled off by the tool point 4 upon withdrawing the dilating instrument 1 in the axial direction.

In addition, even if the elastic synthetic casing 11 is graphically illustrated only in the fifth embodiment shown in FIGS. 8 and 9, synthetic casings 11 of this type can also be used in all other embodiments shown in FIGS. 2 through 7 and previously described.

In addition to the protection of the tool point 4 against impurities, the elastic synthetic casing 11 can be used for shifting the pivotable segments 5 of the tool point 4 from the tool's 4 opened position back into its closed position. In this configuration the return force of the elastic synthetic casing 11 is taken advantage of, after spreading the pivotable segments 5 and the related stretching of the synthetic casing 11, to shift the tool point 4 back into the closed position as soon as the thickened distal end 8 of the actuating element 7 no longer presses the pivotable segments 5 of the tool point 4 into the opened position.

A dilating instrument 1 configured as described above is distinguished in that the dilating mechanism is very resistant because of the mechanism that is powered entirely by lever and pivot points, and in addition it allows the operator a sensitive working because the force applied by the handle 3 arrives in the surgical area essentially free of any play.

What is claimed is:

1. A medical instrument for dilating osseous structures, with a shaft on whose distal end a tool point is positioned and on whose proximal end a handle is positioned, such that the handle and the tool point are in active connection with one another by means of an actuating element in such a way that by actuating the handle the tool point is spreadable radially at least partly and that a distal end of the actuating element is configured as thickened, wherein the tool point consists of several segments that are configured to pivot radially outward by the thickened distal end of the actuating element into a tulip-shaped opened position of the tool point, which is open towards the distal end and wherein the thickened distal end of the actuating element is configured spherical and acts directly on inner surfaces of the pivotable segments and that the pivotable segments essentially completely enclose the thickened distal end of the actuating element when the tool point is in closed position, and wherein the pivotable segments are mounted on a proximal end of the tool point so that the pivotable segments are each configured to pivot about one pivot axis wherein the pivot axes are formed as pivot pins which are mounted in the proximal end of the tool point and which are aligned transverse with respect to the longitudinal axis of the instrument, and wherein, with the tool point in opened position, proximal portions of the pivotable segments are configured with outer sides that are parallel to one another, the parallel configuration limiting slippage of the tool point within the osseous structures, and distal portions of the pivotable segments are configured with outer sides that are oriented inwardly, the proximal portions being portions proximal relative to the distal portions of the pivotable segments.

2. The medical instrument according to claim 1, wherein, in the interior of the tool point made up of the individual segments, an insertion space is configured for the thickened distal end of the actuating element, such that an inner contour of the individual segments of the tool point is configured in such a way that the segments pivot radially outward when the position of the thickened distal end of the actuating element is displaced.

3. The medical instrument according to claim 1, wherein the insertion space is configured as tapering conically in the direction toward the proximal end of the segments.

4. The medical instrument according to claim 1, wherein the tool point consists of three or four pivotable segments.

5. The medical instrument according to claim 1, wherein an outer contour of the distal end of the segments of the tool point, with the tool point in closed position, is configured as conically tapering.

6. The medical instrument according to claim 1, wherein an outer contour of the segments of the tool point, with the tool point in closed position, is configured as conically tapering toward a distal end of the tool point in several stages.

7. The medical instrument according to claim 1, wherein the tool point is removably connected with the shaft.

8. The medical instrument according to claim 1, wherein a portion of the actuating element that is mounted in the tool point is removably coupled by means of a coupling mechanism with a portion of the actuating element that is mounted in the shaft.

9. The medical instrument according to claim 1, wherein the tool point is covered with an elastic synthetic casing to limit penetration of tissue into the tool point in the opened position.

10. The medical instrument according to claim 9, wherein the pivotable segments of the tool point are configured to be shifted from the opened position of the tool point back into the closed position of the tool point by means of the elastic synthetic casing.

11. The medical instrument according to claim 9, wherein the elastic synthetic casing is configured as a covering open at the proximal end, having on its proximal edge a surrounding insulating element.

12. The medical instrument according to claim 11, wherein the insulating element is configured as a surrounding thickening that is configured to be affixed in a corresponding surrounding groove of the tool point.

13. A medical instrument for dilating osseous structures, comprising:
a shaft with a distal end and a proximal end,
a tool point positioned on the distal end, the tool point having a plurality of segments that are configured to pivot radially outward away from one another, and
a handle positioned on the proximal end, the handle and the tool point being in active connection with one another by means of an actuating element such that actuation of the handle spreads the pivotable segments of the tool point radially out, the actuating element having a thickened distal end,
wherein the thickened distal end of the actuating element is spherical and acts directly on inner surfaces of the pivotable segments of the tool point, the pivotable segments essentially completely enclosing the thickened distal end of the actuating element when the tool point is in closed position,
wherein the pivotable segments are mounted on a proximal end of the tool point so that each pivotable segment is configured to pivot about a pivot axis, each pivot axis being formed as a pivot pin mounted in the proximal end of the tool point,
wherein, with the tool point in opened position, proximal portions of the pivotable segments are configured with outer sides that are parallel to one another, the parallel configuration limiting slippage of the tool point within the osseous structures, and distal portions of the pivotable segments are configured with outer sides that are oriented inwardly, the proximal portions being portions proximal relative to the distal portions of the pivotable segments.

* * * * *